(12) United States Patent
Sanders

(10) Patent No.: US 6,638,520 B1
(45) Date of Patent: Oct. 28, 2003

(54) STRUCTURES AND METHODS FOR PROMOTING VASCULARIZATION

(75) Inventor: Joan E. Sanders, Kirkland, WA (US)

(73) Assignee: University of Washington, Seattle, WA (US)

( * ) Notice: Subject to any disclaimer, the term of this patent is extended or adjusted under 35 U.S.C. 154(b) by 132 days.

(21) Appl. No.: 09/885,452

(22) Filed: Jun. 20, 2001

Related U.S. Application Data

(60) Provisional application No. 60/213,734, filed on Jun. 22, 2000.

(51) Int. Cl.$^7$ .............................................. A61L 27/58

(52) U.S. Cl. ................... 424/426; 424/423; 424/583; 623/1.1; 623/1.38; 623/1.42; 623/1.44; 623/1.46; 623/1.47; 623/1.48; 623/2.1

(58) Field of Search ................................. 424/423, 583, 424/426; 623/1.1, 1.38, 1.42, 1.44, 1.46, 1.47, 1.48, 2.1

(56) References Cited

PUBLICATIONS

Demarchez, M. et al., "The role of fibroblasts in dermal vascularization and remodeling of reconstructed human skin after transplantation onto the nude mouse," *Transplantation*, 54:317–326 (1992).

Nguyen, M. et al., "Quantitation of angiogenesis and anti-angiogenesis in the chick embryo chorioallantoic membrane," *Microvacular Research*, 47:31–40 (1994).

Medalie, D.A., et al., "Evaluation of Acellular Human Dermis as a Dermal analog in a composite skin graft," *ASAIO Journal*, 42:M455–M462 (1996).

*Primary Examiner*—Jean C. Witz
(74) *Attorney, Agent, or Firm*—Christensen O'Connor Johnson Kindness PLLC

(57) ABSTRACT

One aspect of the present invention provides implantable medical devices that comprise: (a) a device body; and (b) a surface layer attached to at least a portion of the device body, the surface layer comprising: (1) a surface layer body that defines an internal surface attached to the device body, and an external surface; and (2) a multiplicity of blood vessels disposed within the surface layer body, the blood vessels opening onto the external face of the surface layer body. The present invention also provides synthetic biocompatible materials, methods for making synthetic biocompatible materials, and methods for making implantable medical devices.

19 Claims, 3 Drawing Sheets

STRUCTURES AND METHODS FOR PROMOTING VASCULARIZATION

RELATED APPLICATIONS

The present application claims benefit of priority from U.S. Provisional Patent Application Serial No. 60/213,734, filed on Jun. 22, 2000, under 35 U.S.C. §119, the disclosure of which application is incorporated herein in its entirety.

GOVERNMENT RIGHTS

The invention disclosed in the present application was funded, in part, by Grant No. EEC-9529161 from the National Science Foundation. The Federal government has certain rights in this invention.

FIELD OF THE INVENTION

This invention relates to implantable medical devices, such as implantable medical devices that include a surface layer that promotes vascularization.

BACKGROUND OF THE INVENTION

A limitation of implanted medical devices is the rejection of the material by a process known as the foreign body response. Initially, inflammatory cells, especially macrophages, perceive the surface of most implanted materials as foreign, or as non-natural. These cells initiate a cascade of cellular and tissue reactions leading to a physiological state of chronic inflammation and fibrous encapsulation of the implanted device. In its mature form, the fibrous capsule prevents both humoral and cellular communication with the surrounding tissue.

One way to mitigate this problem is to promote the vascularization of the tissue surrounding the implanted device. In one aspect, the present invention provides biocompatible materials that can be applied to implantable medical devices to promote surface vascularization of the implanted device, thereby reducing or eliminating the foreign body reaction. The present invention also provides methods of making the biocompatible materials.

SUMMARY OF THE INVENTION

In one aspect, the present invention provides implantable medical devices comprising: (a) a device body; and (b) a surface layer attached to at least a portion of the device body, the surface layer comprising: a surface layer body that defines an internal surface, attached to the device body, and an external surface; and a multiplicity of blood vessels disposed within the surface layer body, the blood vessels opening onto the external surface of the surface layer body. Typically, the surface layer is attached to the device body at the location(s) on the device body which are known to stimulate a foreign body reaction, or are likely to stimulate a foreign body reaction.

In another aspect, the present invention provides methods of making implantable medical devices. The methods of this aspect of the invention comprise the steps of: (a) contacting an angiogenic biological material with a biocompatible material under conditions that enable the growth of blood vessels from the angiogenic biological material into the biocompatible material; (b) separating the biocompatible material from the angiogenic biological material under conditions that retain within the biocompatible material at least a portion of the blood vessels that have grown into the biocompatible material; and (c) incorporating the biocompatible material prepared in accordance with steps (a) and (b) into an implantable medical device.

In another aspect, the present invention provides synthetic biocompatible materials comprising: (a) a substrate defining at least one surface, provided that the substrate is not collagen; and (b) a multiplicity of blood vessels disposed within the substrate, the blood vessels opening onto at least one surface of the at least one substrate surface.

The synthetic biocompatible materials of the invention are useful, for example, for making the surface layer of the implantable medical devices of the invention. The implantable medical devices of the invention are useful, for example, in any situation where it is desired to reduce the foreign body reaction to an implanted medical device.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Unless specifically defined herein, all terms used herein have the same meaning as they would to one skilled in the art of the present invention.

As used herein, the term "implantable medical device" refers to a device that is completely or partially implanted into an animal body (such as a human body) during the course of normal operation of the device.

As used herein, the term "angiogenic biological material" refers to biological material capable of growing blood vessels. An example of an angiogenic biological material is the chorioallantoic membrane of a domestic chicken's egg.

In one embodiment, the present invention provides implantable medical devices comprising: (a) a device body; and (b) a surface layer attached to at least a portion of the device body, the surface layer comprising: (1) a surface layer body that defines an internal surface attached to the device body, and an external surface; and (2) a multiplicity of blood vessels disposed within the surface layer body, the blood vessels opening onto the external surface of the surface layer body. Typically, the surface layer is attached to the device body at the locations on the device body where it is desired to reduce or eliminate the foreign body reaction.

Some implantable medical devices of the invention are completely implanted into a living body (i.e., the entire device is implanted within a living body), while some implantable medical devices are partially implanted into a body (i.e., only part of the device is implanted within a living body, the remainder of the device being located outside of the living body). Further, some implantable medical devices include both living tissue and non-living material. Representative examples of implantable medical devices include, but are not limited to: drug delivery devices (such as drug delivery devices comprising a hydrogel surrounded by a porous material), prosthetic devices (such as artificial hip joints and artificial knee joints), cardiovascular devices (such as vascular grafts and artificial heart valves), artificial blood vessels, skin substitutes (such as dermal and epidermal scaffolds), scaffolds that support tissue growth (in such anatomical structures as bone, tooth, nerves, pancreas, eye, and muscle), implantable biosensors (such as those used to monitor the level of drugs within a living body, or the level of blood glucose in a diabetic patient), and percutaneous devices (such as catheters) that penetrate the skin and link a living body to a medical device, such as a kidney dialysis machine.

Figure 1:
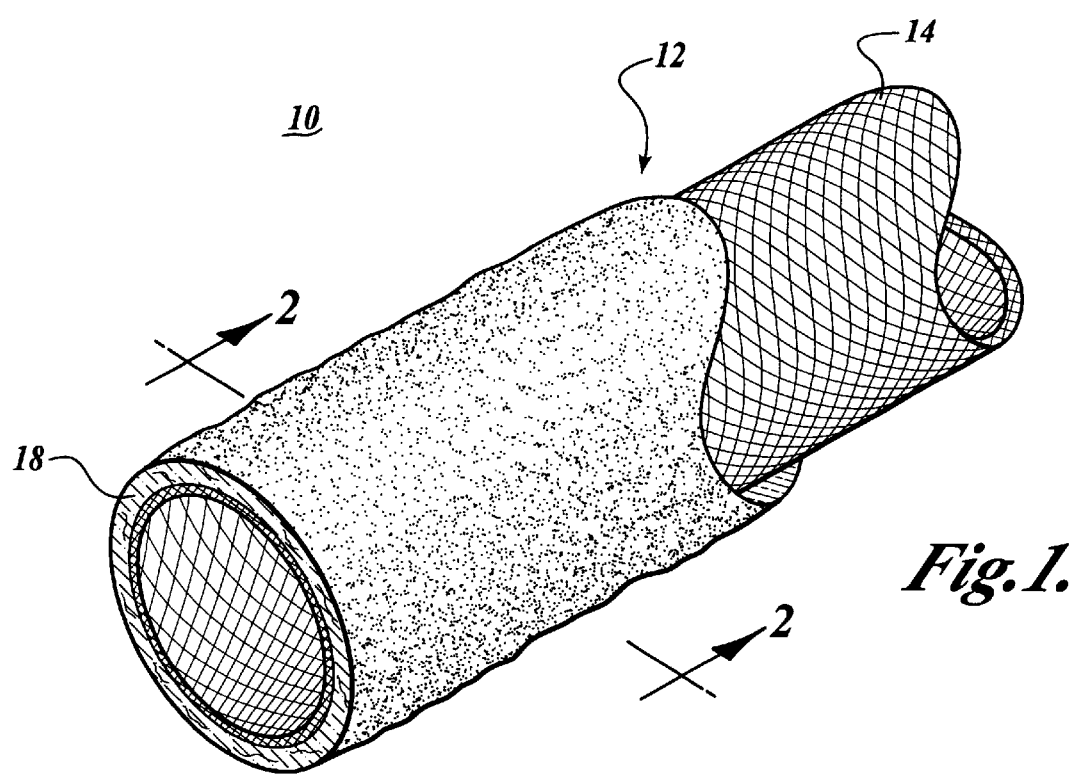
FIG. 1 shows a perspective view of a portion of an artificial blood vessel with the surface layer partially removed.

FIG. 1 shows a representative implantable medical device 10 of the present invention in the form of a portion of artificial blood vessel 12. Artificial blood vessel 12 includes a device body 14 made from a Dacron® mesh. Device body 14 defines a lumen 16. A surface layer 18 is attached to device body 14 and is concentrically disposed therearound. As shown more clearly in the cross section of artificial blood vessel 12 shown in FIG. 2, surface layer 18 includes a surface layer body 20 that defines an internal surface 22 attached to device body 14, and an external surface 24. As shown more clearly in the three-dimensional segment of surface layer body 20 shown in FIG. 3, a multiplicity of blood vessels 26 are disposed within surface layer body 20. Blood vessels 26 each include a first end 28 and a second end 30, and first end 28 of each blood vessel 26 opens onto external face 24 of surface layer 18 forming openings 32 thereon. Blood vessels 26 can be disposed at any angle, and in any conformation, within surface layer body 20. The representative blood vessels 26 shown in FIG. 2 completely penetrate surface layer body 20, but blood vessels 26 do not have to completely penetrate surface layer body 20.

Figure 2:
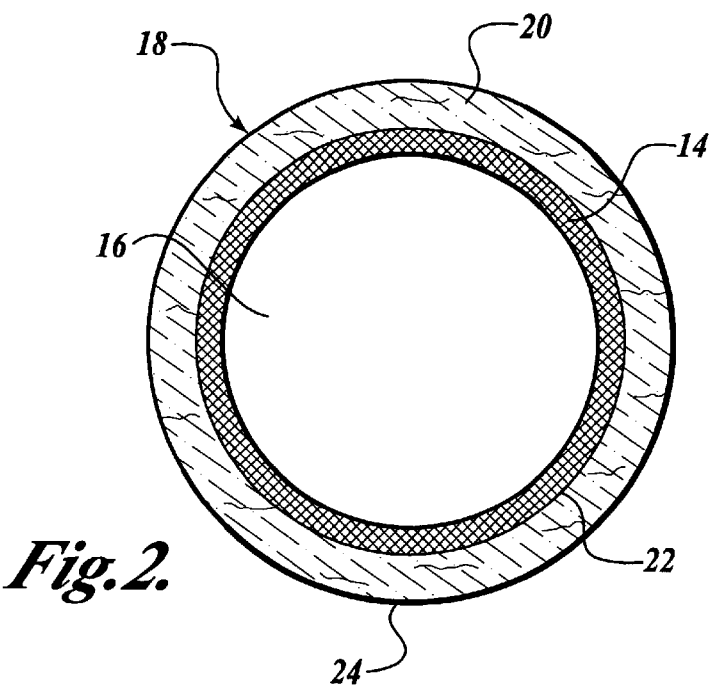
FIG. 2 shows a transverse cross-section of the implantable blood vessel shown in FIG. 1.
Figure 3:
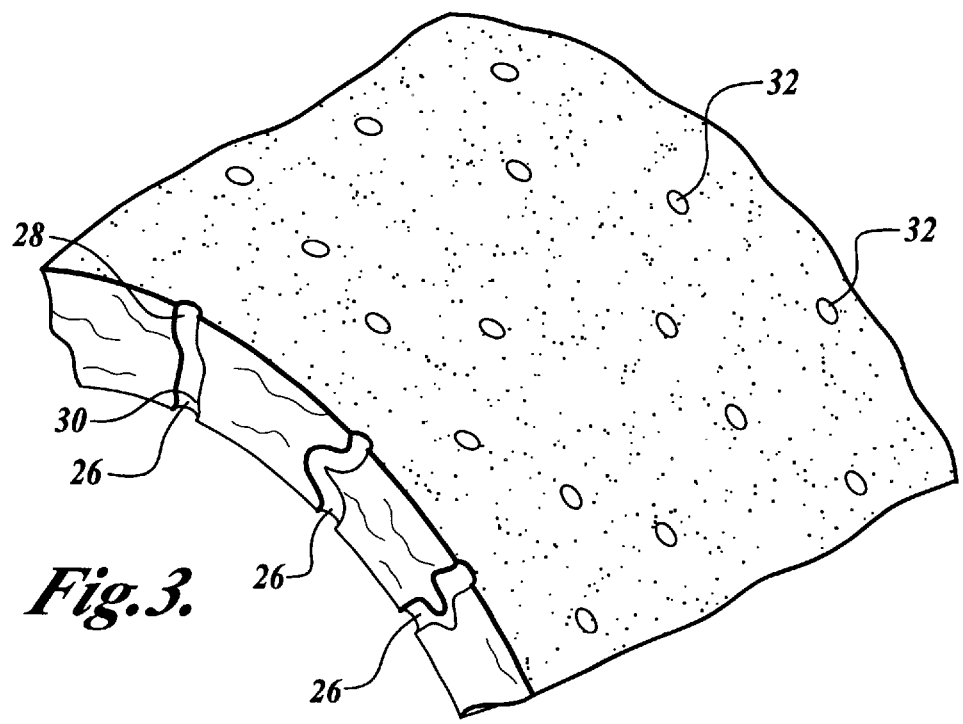
FIG. 3 shows a three-dimensional view of a segment of the surface layer of the implantable, artificial, blood vessel shown in FIGS. 1 and 2.
Figure 4:
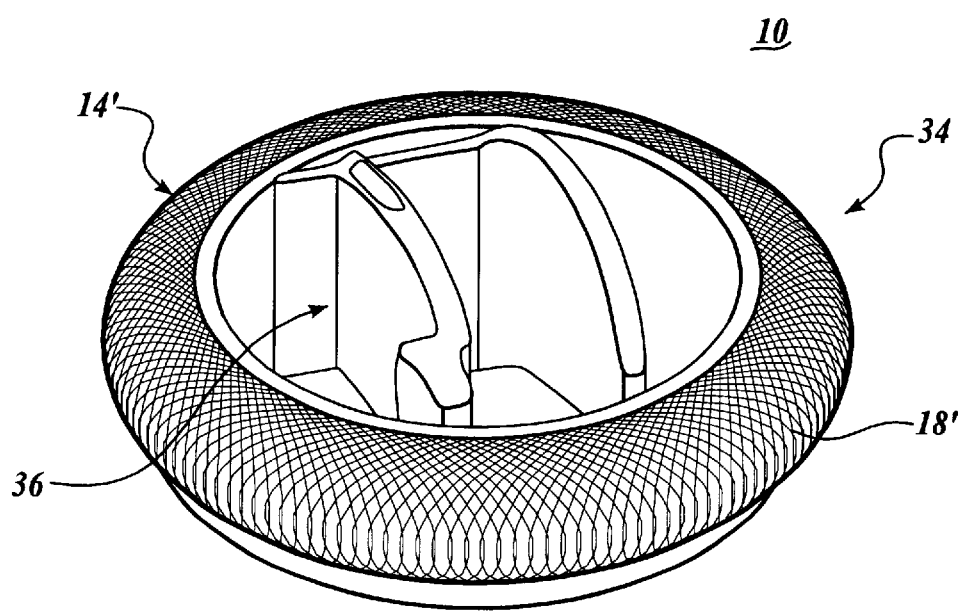
FIG. 4 shows a representative artificial heart valve of the invention.

FIG. 4 shows a representative implantable medical device 10 of the present invention in the form of an implantable artificial heart valve 34. Structures shown in FIG. 4 that are also shown in FIGS. 1–3 are given the same number as those structures in FIGS. 1–3 but with the addition of a prime ('). Artificial heart valve 34 includes a valve assembly 36 disposed within an annular device body 14'. Attached to a portion of annular device body 14' is surface layer 18' within which are disposed a multiplicity of blood vessels 26' (not shown).

The remarks that follow make reference to the parts numbers utilized in the description of the representative implantable medical devices 10 shown in FIGS. 1–4. It is understood, however, that the remarks that follow are applicable to any medical device 10 of the invention. Device body 14 can be made from any suitable material, such as polymers that are known by those of ordinary skill in the art to be useful in constructing implantable medical devices. Representative examples of such polymers include: (poly) urethane, (poly)carbonate, (poly)ethylene, (poly)propylene, (poly)lactic acid, (poly)galactic acid, (poly)acrylamide, (poly)methyl methacrylate, polyester and (poly)styrene. Useful natural polymers include: collagen, hyaluronic acid, dermatan sulfate, hydroxyapatite, chondroitin sulfate, laminin and elastin. Degradable polymers can be utilized to make device body 14.

Surface layer 18 can be made from any material into which blood vessels can grow. Representative materials useful for constructing surface layer 18 include collagen, hyaluronic acid, (poly)urethane, (poly)carbonate, (poly) ethylene, (poly)propylene, (poly)lactic acid, (poly)galactic acid, (poly)acrylamide, (poly)methyl methacrylate, (poly) styrene, polyester, dermatan sulfate, hydroxyapatite, chondroitin sulfate, laminin, protein-coated materials, cell-seeded materials, and elastin.

Blood vessels 26 typically have a mean diameter of from 5 $\mu$m to 50 $\mu$m (such as from 10 $\mu$m to 50 $\mu$m). When implantable medical device 10 is implanted into a living body, blood vessels 26 guide and promote the vascularization of surface layer 18 within the host living body. While not wishing to be bound by theory, blood vessels 26 may stimulate vascularization by providing channels of the appropriate diameter and conformation into which new blood vessels can grow from the host body. Further, blood vessels 26 may include biological molecules (such as biological molecules that are normally produced by blood vessels 26) that stimulate the growth of new blood vessels. Thus, when vascularization of implanted medical device 10 is complete, new blood vessels have grown into some or all of blood vessels 26 and will typically completely or partially destroy or displace blood vessels 26. Efficient vascularization of surface layer 18 contributes to reducing the foreign body reaction and enhances the mechanical stability of the newly-formed host vessels, and so promotes acceptance of implanted medical device 10 by the host body.

In another aspect, the present invention provides methods of making biocompatible materials useful for making surface layer 18 of implantable medical devices 10 of the present invention. The methods of this aspect of the invention utilize the observation that stretching an angiogenic biological material promotes the growth of blood vessels. The methods of this aspect of the invention comprise the steps of: (a) contacting an angiogenic biological material with a biocompatible material; and (b) stretching the angiogenic biological material under conditions that stimulate or enhance the growth of blood vessels from the angiogenic biological material into the biocompatible material (i.e., amount and/or density of blood vessel growth into the biocompatible material from the angiogenic biological material is greater from stretched angiogenic biological material than from unstretched angiogenic biological material).

Angiogenic biological materials useful in this aspect of the invention are capable of growing blood vessels. Representative angiogenic biological materials include the chorioallantoic membrane of birds' eggs, aortic tissue (see, e.g., Nicosa R. F. and Ottinetti A., *Lab. Invest.*, 63(1):115–122 (1990)), rabbit cornea and hamster cheek pouch (see, e.g., Folkman J., *Perspect. Biol. Med.*, 29(1):10–36 (1985), and Gullino, P. M., "Angiogenesis Factors," in *Handbook of Experimental Pharmacology*, edited by R. Baserga, New York, Springer Verlag (1981)).

The angiogenic biological material is subjected to physical stress for a period of time sufficient to stimulate or enhance the growth of blood vessels from the angiogenic biological material into the biocompatible material. The applied physical stress stretches the angiogenic biological material, typically by no more than ten percent of its unstretched length (e.g., a 1 cm length of angiogenic biological material is typically stretched to a length no greater than 1.1 cm). The angiogenic biological material can be stretched in one or more desired directions. For example, as described more fully in Example 1 herein, the angiogenic biological material can be stretched in a uniaxial direction (for example, by grasping an angiogenic biological material at two locations that are directly opposite each other, and pulling in opposite directions). Again, by way of example, in the case of artificial blood vessel 12, or other hollow, implantable, medical device 10 of the invention, the angiogenic biological material can be wrapped around a hollow device body which can be filled with a fluid to which pressure is applied in order to exert a radial stretching force on the angiogenic biological material.

Typically, the stretching force is applied cyclically, such as with a period of from one hour to one week, such as from 2 hours to 24 hours (i.e., the stretching force is applied, for example, for a period of from one hour to one week, the, stretching force is terminated, then reapplied, such as for a period of from one hour to one week). Many cycles (such as, 2, 4, 6, 8 or 10) of stretching can be applied. During stretching the frequency of application of the stretching force is typically 0.01–10.0 Hertz. The stretching force can be applied in several directions simultaneously (such as in two, four or six directions). Moreover, in some embodiments a constant stretching force is applied which is cyclically increased.

In another aspect, the present invention provides synthetic biocompatible materials comprising: (a) substrate defining at least one surface, provided that the substrate is not collagen; and (b) a multiplicity of blood vessels disposed within the substrate, the blood vessels extending from at least one surface into the substrate.

In another aspect, the present invention provides methods of making an implantable medical device. The methods of this aspect of the invention comprise the steps of: (a) contacting an angiogenic biological material with a biocompatible material under conditions that enable the growth of blood vessels from the angiogenic biological material into the biocompatible material; (b) separating the biocompatible material from the angiogenic biological material under conditions that retain within the biocompatible material at least a portion of the blood vessels that have grown into the biocompatible material; and (c) incorporating the biocompatible material prepared in accordance with steps (a) and (b) into an implantable medical device.

In some embodiments, at least 25% (such as at least 50%, or at least 70%, or at least 80%, or at least 90%) of the blood vessels that have grown into the biocompatible material are retained therein after the biocompatible material is separated from the angiogenic biological material. In the methods of this aspect of the invention, in some embodiments the angiogenic biological material is subjected to a physical stress that stretches the angiogenic biological material by up to 10% of its unstretched length. In other embodiments, the angiogenic biological material is stretched up to 50% of its unstretched length (e.g., up to 20%, or 30% or 40% of its unstretched length). The physical stress is applied to the angiogenic biological material while the angiogenic biological material is in contact with the biocompatible material, thereby promoting the growth of blood vessels into the biocompatible material from the angiogenic material. In some embodiments of the methods of this aspect of the invention, the angiogenic biological material is cyclically stretched. The angiogenic biological material can be stretched in numerous directions, such as in two directions, four directions, or six directions. The biocompatible material can also include one or more types of molecules that promote angiogenesis.

Figure 5:
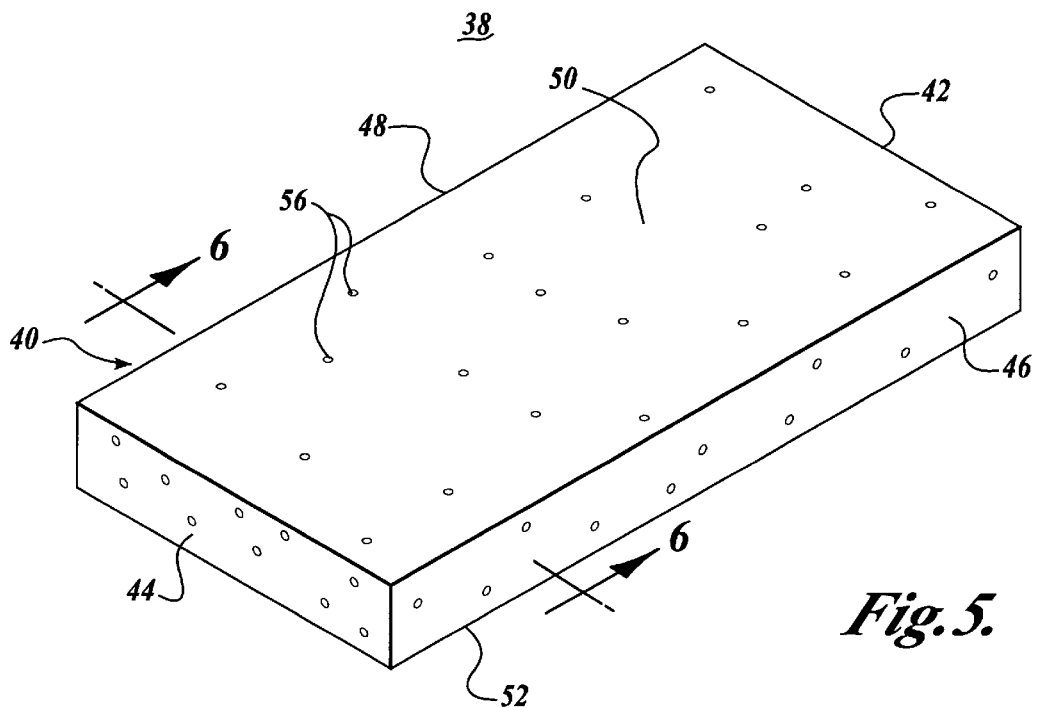
FIG. 5 shows a representative drug delivery device of the invention.
Figure 6:
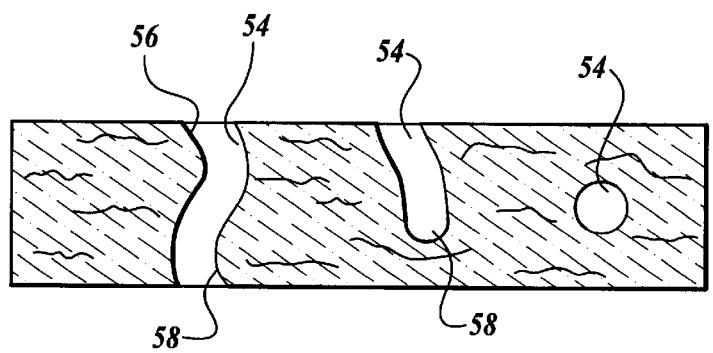
FIG. 6 shows a transverse cross section of the representative drug delivery device shown in FIG. 5.

In another embodiment, the present invention provides implantable medical devices comprising: (a) a body that defines at least one external surface; and (b) a multiplicity of blood vessels disposed within the body, the blood vessels each opening onto at least one external surface of the body. FIG. 5 shows a representative embodiment of an implantable medical device of this aspect of the invention in the form of drug delivery device 38 which includes a body 40 defining a first end 42, a second end 44, a first face 46, a second face 48, an upper surface 50, and a lower surface 52. Disposed within drug delivery device body 40 are a multiplicity of blood vessels 54 shown more clearly in FIG. 6. Blood vessels 54 include a first end 56 and a second end 58. At least one of first end 56 or second end 58 open onto drug delivery device body first end 42, second end 44, first face 46, second face 48, upper surface 50, or lower surface 52. Blood vessels 54 can be disposed in any conformation within drug delivery device body 40. Representative examples of implantable medical devices of this aspect of the invention include drug delivery devices and artificial skin. Implantable medical devices of this aspect of the invention can be made from the same materials that are useful for making surface layer 18 of implantable medical devices 10 described herein. The implantable medical devices of this aspect of the invention can be made in accordance with the methods of making biocompatible materials useful for making surface layer 18 of implantable medical devices 10 of the present invention.

While the preferred embodiment of the invention has been illustrated and described, it will be appreciated that various changes can be made therein without departing from the spirit and scope of the invention.

EXAMPLE 1

This example describes the preparation of a synthetic biocompatible material useful as surface layer 18 of implantable medical devices 10.

Quail eggs were cultured in a manner similar to that used for chicken embryo (Auerbach et al., *Dev. Biol.* 41:391–394 (1974)). Fertilized quail eggs (Northwest Gamebirds, Kennewick, Wash.) were placed horizontally in a thermally-controlled incubator (2200, VWR Scientific Products, Seattle, Wash.) at 37° C. for three days. The eggs were then sprayed with 70% ethanol solution, wiped with betadine, and allowed to dry in a tissue culture hood. Each embryo was then placed in a 50 mm diameter polystyrene culture dish by making a longitudinal incision in the shell with sterile scissors, applying pressure to the ends of the egg, and then releasing the embryo into the dish. The embryos in the 50 mm diameter culture dishes were then placed in larger 150 mm polystyrene tissue culture dishes with 5 ml of distilled water to maintain humidity. The incubation period was seven days, bringing the total incubation period to ten days.

On the tenth day of incubation, collagen gels containing an angiogenic reagent (basic fibroblast growth factor, bFGF) were placed on the chorioallantoic membrane (CAM) using methods and concentrations similar to those described by Nguyen et al. (*J. Microvasc. Res.*, 47:31–40, 1994). These gels were made by combining bFGF (Sigma, St. Louis, Mo.) and 20 mg of sterilized aluminum sucrose octasulfate (Sucralfate, Sigma, St. Louis, Mo.) in 200 $\mu$l of 1 mg/ml bovine serum albumin (BSA, Sigma, St. Louis, Mo.). To this mixture 400 $\mu$l of neutralized (pH 7.4) type I collagen solution (Vitrogen, Cohesion, Palo Alto, Calif.) was added. The final solution was kept at 0° C. to avoid premature gelation. The final concentration of bFGF in solution was 0.31 $\mu$M. Twenty $\mu$l of the solution was pipetted onto a 4×4 mm sterile nylon mesh (Small Parts Inc., Miami Lakes, Fla.). An additional 40 μl of solution was pipetted onto a small section of a 4 mm wide strip of elastomeric, porous polyurethane (3M Corporation, St. Paul, Minn.). The pore size of the polyurethane was in the range of 100–200 microns, as estimated by light microscopy. Collagen solution was aspirated through the material several times to ensure that it had completely permeated the pores. The strip was then placed on top of the nylon mesh with the 20 μl of collagen. The mesh and strip were then placed in an incubator at 37° C. and the collagen was allowed to gel for several hours. Control gels were made in a similar manner with the exception that a 4×4 mm square of the polyurethane replaced the polyurethane strip.

One control gel and one test gel were implanted on a CAM. The gels were placed 2–3 mm to the left and right of the central anterior vitelline vein in the outer third of the CAM. This location was identical to that used by Nyugen, supra, who demonstrated reproducible results for this location. Following implantation, the CAM in the 50 mm diameter culture dish was placed in a 100 mm diameter tissue culture dish, modified to allow the elastomeric strip to pass through the edges of the dish. Distilled water was placed in the dish to maintain humidity. The embryos were placed in the incubator for two more days and then transferred to a custom mechanical loading device.

The loading device was a closed-loop system capable of either force or displacement control in a thermally-controlled sterile environment, and is disclosed in Mitchell, S. B. et al., *IEEE Trans. Biomed. Engi.* 48(2):268:–273 (2001) which publication is incorporated herein by reference.

Briefly, voice coil actuators connected to the edges of a material sample through steel rods and connecting frames applied user-specified displacements to the specimen. The system was operated in uniaxial mode to apply sinusoidal displacements at 1 Hz and 1% strain amplitude at 37° C. The 1% strain level was selected as a tradeoff between that sufficient to induce a response but low enough so as not to sever the membrane and destroy the CAM. Similar strain level were used by Yang et al. (*J. Biol. Chem.* 273:6550–6555 (1998)) to show that small deformations can selectively suppress MMP-1 synthesis by vascular smooth muscle cells. The use of only one strain level here was appropriate since only comparison of strained to unstrained samples was of interest in this investigation. The applied 1% strain was measured relative to the ends of the polyurethane strip, and was not necessarily reflective of that in the stressed collagen gel. Because the ends of the polyurethane strip next to the connecting rods were stiffer than the central region, strains in the polyurethane over the collagen gel would be expected slightly higher than 1%. Strain was applied for one hour followed by a four-hour rest period. This straining pattern was repeated for 24 hours (starting with a loading period).

The polyurethane material was then carefully removed from each gel. Visual inspection demonstrated approximately identical dimensions for each gel from the same CAM. Images were taken of each gel using a MicroPhot-2A light microscope (Nikon, Inc., Melville, N.Y.), digital data acquisition system (Optronics, Goleta, Calif.), and Image-Pro Plus software (Media Cybernetics, Carlsbad, Calif.). Vessel density was assessed using a point counting method (Bolender, R. P. et al., *Am. J. Physiol.*, 265:L521–L548, 1993) which allowed statistical comparison of the strained gel region with the unstrained gel region for each CAM. The image data from each gel was divided into a total of at least 50 identical boxes. A grid of dots was superimposed over each box, and the number of dots on vessels was counted and converted to a percentage (dots on vessels/total dots) for each box. This measurement was equal to the percentage area covered by vessels (vessel area/total area). The number of boxes selected (at least 50 for each gel) was such that the coefficient of error (CE) value for each gel was less than 0.05, a threshold value appropriate for morphological analysis (Bolender, R. P. et al., supra). The hypothesis that the strained gel had a greater vessel density than the control gel was tested for each CAM. A one-tailed t-test was used to evaluate the null hypothesis.

For each of the embryos tested, the strained gel had a statistically significant increase in percent area of the gel occupied by blood vessels compared with the control gel (TABLE 1). The magnitude of the increase ranged from 13.2% to 27.2%. These results support the hypothesis that mechanical strain has an angiogenic effect on blood vessels. They also suggest that this model is effective for mimicking the strain-sensitive angiogenic effect.

Table 1. Comparison of percentage of the gel occupied by blood vessels for control and mechanically strained gels from the CAM assay for mechanical loading. At least 50 samples were taken for each of the two gels in each CAM. S.D=standard deviation

| CAM Number | Vessel Percent Area for Strained Gel (Mean ± S.D.) | Vessel Percent Area for Control Gel (Mean ± S.D.) | Difference in Mean Vessel Percent Area | P-Value from Vessel Area Comparison |
| --- | --- | --- | --- | --- |
| 1 | 42.4 ± 22.9% | 15.2 ± 15.1% | 27.2% | $1.1 \times 10^{-7}$ |
| 2 | 46.3 ± 26.4% | 30.8 ± 27.4% | 15.5% | $2.5 \times 10^{-3}$ |
| 3 | 47.4 ± 16.8% | 23.5 ± 17.7% | 23.9% | $2.3 \times 10^{-10}$ |
| 4 | 57.3 ± 15.1% | 44.2 ± 15.4% | 13.2% | $2.0 \times 10^{-5}$ |

The vessel densities among the four strained samples were comparable (Column 2, Table 1). The increase in vessel density for strained vs. control was greater for the samples with lower control sample vessel densities. The quantity percent increase in mean percent vessel area and the quantity vessel percent area for the control gel fit well to a power relationship. Because the strain applied was approximately consistent among samples (~1% strain), a possible explanation for this response was that the vessels only proliferated to a point consistent with the needs established by the local strain environment; those needs were comparable among the four CAMs.

EXAMPLE 2

This example demonstrates the growth of blood vessels into a synthetic biocompatible material.

Fertilized quail eggs (Coturnix eggs, Northwest Gamebirds, Wash.) were bated in their shells for three days at 36.3° C. On day three the eggs were cracked six well culture plates (well diameter=35 mm) and placed in a humidified incubator (~100% humidity) (36.3° C.) for seven days. On day ten a fibro-porous polyurethane biomaterial incorporating a collagen gel (1.25 mg/ml rat tail collagen I, provided by Dr. Nicosia, University of Washington, Seattle, Wash.) seeded with growth factors VEGF (5 μg/ml) and bFGF (10 μg/ml) was placed on top of the CAM. The biomaterial was supported by a Teflon ring (8 mm outer diameter). The biomaterial was left on the CAM for four days to allow time for vessel ingrowth. On day fourteen the biomaterial was removed and implanted into the rat dorsum for two weeks. After two weeks the samples and surrounding tissue were removed and embedded in OCT (Optimum Cutting Temperature Embedding Media, Tissue-Tek, Sakura, Calif.) in preparation for immunocytochemistry. Serial sections (4–5 μm thick) were taken from the samples and labeled using the primary antibodies: Quail endothelial cells (QH1 mouse anti-quail endothelial cell marker, Developmental Studies Hybridoma Bank, University of Iowa, Iowa), rat endothelial cells (HIS52 RECA-1 Endothelium Pan Marker, Alternative Biomedical Services, Florida ), and rat laminin (2E8 mouse anti-human laminin supernatant, DSHB, Iowa). All sections were labeled using Vectastain Elite ABC Kit (Vecta Laboratories, Burlingame, Calif.) and visualized using DAB (Dako Corporation, Carpinteria, Calif.). Cross-reactivity tests demonstrated no cross-reactivity between species for these three labels.

Results from serial sections showed that rat host vessels grew within the quail vascular structures. Rat vessel internal wall surfaces identified with rat endothelial cell marker were consistently smaller than the quail vessel internal surfaces identified with quail endothelial cell marker. The shapes of the rat and quail vessel walls in nearly all sections were very similar. Rat laminin labeled sections showed shapes similar to those for sections labeled for rat endothelial cells.

The embodiments of the invention in which an exclusive property or privilege is claimed are defined as follows:

1. A method of making an implantable medical device, the method comprising the steps of:
   (a) contacting an angiogenic biological material with a biocompatible material under conditions that enable the growth of blood vessels from the angiogenic biological material into the biocompatible material;
   (b) separating the biocompatible material from the angiogenic biological material under conditions that retain within the biocompatible material at least a portion of the blood vessels that have grown into the biocompatible material; and
   (c) incorporating the biocompatible material prepared in accordance with steps (a) and (b) into an implantable medical device.

2. The method of claim 1, wherein at least 50% of the blood vessels that have grown into the biocompatible material are retained therein after the biocompatible material is separated from the angiogenic biological material.

3. The method of claim 1, wherein the conditions that enable the growth of blood vessels from the angiogenic biological material into the biocompatible material comprise the step of stretching the angiogenic biological material by up to ten percent of its unstretched length.

4. The method of claim 3, wherein the angiogenic biological material is cyclically stretched.

5. The method of claim 3, wherein the angiogenic biological material is stretched in two directions.

6. The method of claim 3, wherein the angiogenic biological material is stretched in four directions.

7. The method of making an implantable medical device of claim 1 wherein the implantable medical device is selected from the group of implantable medical devices consisting of a drug delivery device, a prosthetic device, an artificial blood vessel, a skin substitute, an implantable biosensor and a percutaneous device.

8. A method of making a biocompatible material, the method comprising the steps of:
   (a) contacting an angiogenic biological material with a biocompatible material; and
   (b) stretching the angiogenic biological material under conditions that stimulate or enhance the growth of blood vessels from the angiogenic biological material into the biocompatible material.

9. The method of claim 8 wherein the angiogenic biological material is a chorioallantoic membrane.

10. The method of claim 8 wherein the biocompatible material is a polymer.

11. The method of claim 9 wherein the polymer is selected from the group of polymers consisting of collagen, hyaluronic acid, (poly)urethane, (poly)carbonate, (poly)ethylene, (poly)propylene, (poly)lactic acid, (poly)galactic acid, (poly)acrylamide, (poly)methyl methacrylate, (poly)styrene, polyester, dermatan sulfate, hydroxyapatite, chondroitin sulfate, laminin, protein-coated materials, cell-seeded materials, and elastin.

12. The method of claim 11 wherein the polymer is collagen.

13. The method of claim 11 wherein the polymer is hyaluronic acid.

14. The method of claim 8 wherein the angiogenic biological material is stretched up to ten percent of its unstretched length.

15. The method of claim 8 wherein the angiogenic biological material is stretched up to five percent of its unstretched length.

16. The method of claim 8 wherein the angiogenic biological material is cyclically stretched.

17. The method of claim 8 wherein the angiogenic biological material is stretched in two directions.

18. The method of claim 8 wherein the angiogenic biological material is stretched in four directions.

19. The method of claim 8 wherein the angiogenic biological material is subjected to a radial stretching force.

* * * * *

UNITED STATES PATENT AND TRADEMARK OFFICE
CERTIFICATE OF CORRECTION

PATENT NO. : 6,638,520 B1
DATED : October 28, 2003
INVENTOR(S) : J.E. Sanders

It is certified that error appears in the above-identified patent and that said Letters Patent is hereby corrected as shown below:

Column 4,
Line 13, "theory," should read -- theory, it is noted that --

Column 5,
Line 12, "week, the," should read -- week, the --
Line 14, "such as," should read -- such as --

Column 7,
Line 40, "level were used" should read -- levels were used --

Column 8,
Line 54, "bated" should read -- incubated --
Line 55, "crack six" should read -- cracked into six --

Column 9,
Line 9, "Florida )," should read -- Florida), --
Lines 41 and 45, "claim 1," should rad -- claim 1 --
Line 50, "claim 3," should read -- claim 3 --

Column 10,
Line 24, "claim 9" should read -- claim 10 --

Signed and Sealed this

First Day of June, 2004

JON W. DUDAS
*Acting Director of the United States Patent and Trademark Office*